United States Patent
Ito et al.

(10) Patent No.: US 11,285,462 B2
(45) Date of Patent: Mar. 29, 2022

(54) CATALYST

(71) Applicant: Mitsubishi Chemical Corporation, Chiyoda-ku (JP)

(72) Inventors: Mitsunobu Ito, Chiyoda-ku (JP); Hiroto Ito, Chiyoda-ku (JP)

(73) Assignee: Mitsubishi Chemical Corporation, Chiyoda-ku (JP)

( * ) Notice: Subject to any disclaimer, the term of this patent is extended or adjusted under 35 U.S.C. 154(b) by 126 days.

(21) Appl. No.: 16/690,264

(22) Filed: Nov. 21, 2019

(65) Prior Publication Data
US 2020/0086301 A1 Mar. 19, 2020

Related U.S. Application Data

(63) Continuation of application No. PCT/JP2019/012001, filed on Mar. 22, 2019.

(30) Foreign Application Priority Data

Mar. 23, 2018 (JP) .............................. JP2018-055537

(51) Int. Cl.
| | | |
|---|---|---|
| B01J 23/28 | (2006.01) | |
| B01J 23/31 | (2006.01) | |
| B01J 23/745 | (2006.01) | |
| B01J 23/75 | (2006.01) | |
| B01J 23/755 | (2006.01) | |
| B01J 35/08 | (2006.01) | |
| B01J 35/10 | (2006.01) | |
| C07C 51/16 | (2006.01) | |

(52) U.S. Cl.
CPC .............. B01J 23/28 (2013.01); B01J 23/31 (2013.01); B01J 23/745 (2013.01); B01J 23/75 (2013.01); B01J 23/755 (2013.01); B01J 35/08 (2013.01); B01J 35/1009 (2013.01); B01J 35/1047 (2013.01); B01J 35/1057 (2013.01); B01J 35/1061 (2013.01); B01J 35/1066 (2013.01); C07C 51/16 (2013.01)

(58) Field of Classification Search
CPC . B01J 23/28; B01J 23/31; B01J 23/745; B01J 23/75; B01J 23/755; B01J 35/08; B01J 35/1009; B01J 35/1047; B01J 35/1057; B01J 35/1061; B01J 35/1066; C07C 51/16

See application file for complete search history.

(56) References Cited

U.S. PATENT DOCUMENTS

| | | | |
|---|---|---|---|
| 3,829,476 A | 8/1974 | Yamada et al. | |
| 4,374,759 A * | 2/1983 | Khoobiar ............ | B01J 23/8876 502/249 |
| 4,442,308 A | 4/1984 | Arntz et al. | |
| 4,656,157 A | 4/1987 | Hofmann et al. | |
| 4,873,217 A | 10/1989 | Kawajiri et al. | |
| 5,153,162 A | 10/1992 | Kurimoto et al. | |
| 7,262,148 B2 * | 8/2007 | Teshigahara ........... | B01J 23/002 502/224 |
| 7,473,666 B2 * | 1/2009 | Yanagi .................. | B01J 23/002 502/233 |
| 7,579,501 B2 * | 8/2009 | Teshigahara ........... | B01J 29/048 562/545 |
| 7,632,777 B2 * | 12/2009 | Teshigahara ......... | B01J 35/1009 502/311 |
| 9,604,199 B2 * | 3/2017 | Hiraoka ................. | B01J 23/002 |
| 2003/0187305 A1 | 10/2003 | Petzoldt et al. | |
| 2004/0038820 A1 | 2/2004 | Yunoki et al. | |
| 2004/0058812 A1 | 3/2004 | Yunoki et al. | |
| 2004/0249000 A1 | 12/2004 | Yada et al. | |
| 2006/0201573 A1 | 9/2006 | Petzoldt et al. | |
| 2006/0205978 A1 | 9/2006 | Yunoki et al. | |
| 2008/0107583 A1 * | 5/2008 | Teshigahara ......... | B01J 23/8876 423/263 |
| 2008/0286186 A1 * | 11/2008 | Teshigahara ......... | B01J 23/8876 423/263 |
| 2015/0328623 A1 | 11/2015 | Hiraoka et al. | |
| 2016/0244393 A1 | 8/2016 | Kurakami et al. | |

FOREIGN PATENT DOCUMENTS

| | | |
|---|---|---|
| EA | 200500724 A1 | 8/2005 |
| EP | 0 293 859 A1 | 12/1988 |
| JP | 58-000930 A | 1/1983 |

(Continued)

OTHER PUBLICATIONS

Taiwanese Office Action dated Jan. 14, 2020, in Patent Application No. 108110099, citing document AO therein, 12 pages (with unedited computer generated English translation and English Translation of Category of Cited Documents).

International Search Report dated May 7, 2019 in PCT/JP2019/012001 filed on Mar. 22, 2019.

Extended European Search Report dated Apr. 20, 2021 in European Patent Application No. 19772527.8, citing document AO therein, 7 pages.

Office Action issued in the corresponding RU patent No. 2019138456 dated Nov. 25, 2021 (with English translation).

Office Action issued in the corresponding IN application No. 201917049346 dated Dec. 31, 2021.

*Primary Examiner* — Cam N. Nguyen

(74) *Attorney, Agent, or Firm* — Oblon, McClelland, Maier & Neustadt, L.L.P.

(57) ABSTRACT

A catalyst for producing unsaturated aldehyde and unsaturated carboxylic acid, wherein the cumulative pore volume (A) of pores having a pore diameter of 1 μm or more and 100 μm or less, in the catalyst, is 0.12 ml/g or more and 0.19 ml/g or less, and the ratio (A/B) of the cumulative pore volume (A) to the cumulative pore volume (B) of pores having a pore diameter of 1 μm or more and 100 μm or less, in a pulverized product not passing through a Tyler 6 mesh, in a pulverized product obtained by pulverization of the catalyst under a particular condition is 0.30 or more and 0.87 or less.

7 Claims, No Drawings

(56) References Cited

FOREIGN PATENT DOCUMENTS

| | | |
|---|---|---|
| JP | 61-141933 A | 6/1986 |
| JP | 63-200839 A | 8/1988 |
| JP | 03-086242 A | 4/1991 |
| JP | 2004-136267 A | 5/2004 |
| JP | 2004-515337 A | 5/2004 |
| JP | 2008-535646 A | 9/2008 |
| JP | 2015-096497 A | 5/2015 |
| JP | 2017-176931 A | 10/2017 |
| SU | 574143 A3 | 9/1977 |
| TW | 201512164 A | 4/2015 |
| WO | WO 2013/161702 A1 | 10/2013 |

\* cited by examiner

CATALYST

CROSS-REFERENCE TO RELATED APPLICATION

This is a continuation of International Application PCT/JP2019/012001, filed on Mar. 22, 2019, and designated the U.S., and claims priority from Japanese Patent Application 2018-055537 which was filed on Mar. 23, 2018, the entire contents of which are incorporated herein by reference.

TECHNICAL FIELD

The present invention relates to a catalyst for producing unsaturated aldehyde and unsaturated carboxylic acid.

BACKGROUND ART

Catalysts containing molybdenum as an essential component are generally used as catalysts for producing unsaturated aldehyde and unsaturated carboxylic acid by catalytic gas phase oxidation of olefin having 3 or 4 carbon atoms and oxygen-containing gas. Specifically, catalysts for use in production of acrolein and acrylic acid from propylene and the like as raw materials, catalysts for use in production of methacrolein and methacrylic acid from isobutylene and the like as raw materials, and production methods thereof have been actively and progressively improved from various viewpoints.

Methods of producing unsaturated aldehyde or unsaturated carboxylic acid involve catalytic gas phase oxidation of olefins and oxygen-containing gases in fixed-bed reactors filled with catalysts.

Such catalysts with which fixed-bed reactors are filled have any shape such as a cylinder shape, a ring shape, a tablet shape, or a spherical shape, and such catalysts commonly used are catalysts obtained by molding powders of catalytically active components or catalysts including catalytically active components supported on inert carriers having the same shape as described above.

Patent Literature 1 presents a catalyst including molybdenum, iron and bismuth, and having a particular specific surface area and a particular pore volume, as a catalyst for oxidation of propylene. Patent Literature 2 discloses a catalyst for producing unsaturated aldehyde and unsaturated carboxylic acid, in which the pore volume with respect to a particular pore diameter is in a particular range.

PRIOR ART DOCUMENTS

Patent Literature

Patent Literature 1: JP S63-200839 A
Patent Literature 2: JP 2017-176931 A

SUMMARY OF THE INVENTION

Technical Problem

However, the catalyst described in Patent Literature 1 is not sufficient in reaction efficiency even in catalytic gas phase oxidation of olefin such as propylene and oxygen-containing gas by using the catalyst, and cannot provide unsaturated aldehyde such as acrolein and unsaturated carboxylic acid such as acrylic acid at high yields. Moreover, the catalyst has the problem of causing a side reaction to occur in catalytic gas phase oxidation at high temperatures for an enhancement in activity of the catalyst, resulting in more reductions in yields. Furthermore, the catalyst is also not sufficient in strength, and the catalyst can be powdered and/or cracked, thereby causing a catalytic gas phase oxidation reaction not to be stably and efficiently performed for a long period.

The catalyst described in Patent Literature 2 also has room for improvements in the yield of unsaturated carboxylic acid and the strength of the catalyst.

The present invention has been made in order to solve the above problems. That is, an object is to provide a catalyst which is excellent in conversion rate of a raw material being olefin such as propylene and can allow for selective production of desired unsaturated aldehyde and unsaturated carboxylic acid at high yields even under a condition of a large amount of the raw material fed, namely, a high load applied to the catalyst, and which is high in strength and can allow for a stable catalytic gas phase oxidation reaction for a long period, as a catalyst for use in catalytic gas phase oxidation of olefin such as propylene and oxygen-containing gas and thus production of corresponding unsaturated aldehyde such as acrolein and corresponding unsaturated carboxylic acid such as acrylic acid.

Solution to Problem

The present inventors have made intensive studies in order to solve the above problems, and as a result, have found that a catalyst can be made in which the cumulative pore volume (A) of pores having a pore volume of 1 µm or more and 100 µm or less, in the catalyst, is 0.12 ml/g or more and 0.19 ml/g or less and the ratio (A/B) of the cumulative pore volume (A) to the cumulative pore volume (B) of pores having a pore diameter of 1 µm or more and 100 µm or less, in a pulverized product not passing through a Tyler 6 mesh, in a pulverized product obtained by pulverization of the catalyst under a particular condition is 0.30 or more and 0.87 or less, to thereby allow for an excellent conversion rate of olefin, and favorable selectivity of unsaturated aldehyde such as acrolein and favorable selectivity of unsaturated carboxylic acid such as acrylic acid, in particular, high selectivity ratio of unsaturated carboxylic acid such as acrylic acid, as well as enhanced yields of unsaturated aldehyde such as acrolein and unsaturated carboxylic acid such as acrylic acid, even under conditions of a large amount of olefin fed and a high load applied to the catalyst in catalytic gas phase oxidation of olefin and oxygen-containing gas by using the catalyst, thereby leading to the present invention.

That is, the present invention is as follows.

[1] A catalyst for producing unsaturated aldehyde and unsaturated carboxylic acid, wherein the cumulative pore volume (A) of pores having a pore diameter of 1 µm or more and 100 µm or less, in the catalyst, is 0.12 ml/g or more and 0.19 ml/g or less, and the ratio (A/B) of the cumulative pore volume (A) to the cumulative pore volume (B) of pores having a pore diameter of 1 µm or more and 100 µm or less, in a pulverized product not passing through a Tyler 6 mesh, in a pulverized product obtained by pulverization of the catalyst under a pulverization condition A is 0.30 or more and 0.87 or less; Pulverization condition A one hundred g of the catalyst is charged into a tumbling granulator which comprises a cylindrical body vertically secured and a disk horizontally disposed at a lower end of the cylindrical body and which allows for rotation movement and revolution movement of a particle by rotation of the disk around the center of the cylindrical body, operation of the disk is started at a relative centrifugal acceleration of 12 G and accelerated to a relative centrifugal acceleration of 130 G over 1 minute, and rotation of the disk is continued at a relative centrifugal acceleration of 130 G for 2 minutes; wherein the relative centrifugal acceleration is defined as a numerical value expressed as the ratio of the magnitude of a centrifugal force applied to a unit weight of the catalyst, to gravity acceleration, and is represented by the following Equation (X):

$$F=1118 \times r \times N^2 \times 10^{-8} \qquad \text{Equation (X)}$$

F: relative centrifugal acceleration (G),
r: distance (cm) from center of rotation to lower end of cylindrical body,
N: rate of rotation (rpm).

[2] The catalyst according to [1], wherein the catalyst comprises molybdenum (Mo), bismuth (Bi), cobalt (Co), nickel (Ni) and iron (Fe), and the atomic ratio among molybdenum (Mo), bismuth (Bi), cobalt (Co), nickel (Ni) and iron (Fe) in the catalyst satisfies the following Formula (1):

$$Mo_aBi_bCo_cNi_dFe_e \qquad (1)$$

wherein a to e represent the atomic ratio with respect to each of elements, and ranges of b=0.5 to 7, c=0.1 to 10, d=0.1 to 10 and e=0.05 to 5 are satisfied when a=12.

[3] The catalyst according to [1] or [2], wherein the catalyst comprises a carrier.
[4] The catalyst according to any one of [1] to [3], wherein the catalyst has a spherical shape.
[5] A method for producing acrolein and acrylic acid, wherein the method comprises a step of performing catalytic gas phase oxidation of propylene and oxygen-containing gas by using the catalyst according to any one of [1] to [4].

Advantageous Effects of Invention

The present invention can provide a catalyst which is high in catalyst performance, which is excellent in conversion rate of olefin even under a condition of a high load applied to the catalyst, and furthermore which can allow for production of unsaturated aldehyde such as acrolein and unsaturated carboxylic acid such as acrylic acid at high selectivities with an excessive oxidation reaction being suppressed. Furthermore, the catalyst according to the present invention is high in strength and is less powdered. As a result, the catalyst can be efficiently packed in a reactor, and the catalyst can be utilized to thereby allow for production of unsaturated aldehyde such as acrolein and unsaturated carboxylic acid such as acrylic acid, in particular, unsaturated carboxylic acid such as acrylic acid at high selectivities over a long period from the beginning of catalytic gas phase oxidation.

DESCRIPTION OF EMBODIMENTS

Hereinafter, modes for carrying out the present invention will be described in detail, but the description of each component set forth below is typically illustrative of embodiments of the present invention, and the present invention is not intended to be limited to the content of the description.

[Catalyst]
A catalyst according to one embodiment of the present invention is a catalyst for producing unsaturated aldehyde and unsaturated carboxylic acid, wherein the cumulative pore volume (A) of pores having a pore diameter of 1 μm or more and 100 μm or less, in the catalyst, is 0.12 ml/g or more and 0.19 ml/g or less, and the ratio (A/B) of the cumulative pore volume (A) to the cumulative pore volume (B) of pores having a pore diameter of 1 μm or more and 100 μm or less, in a pulverized product not passing through a Tyler 6 mesh, in a pulverized product obtained by pulverization of the catalyst under a pulverization condition A is 0.30 or more and 0.87 or less. The ratio (A/B) is preferably 0.50 or more and 0.87 or less, more preferably 0.60 or more and 0.87 or less, further preferably 0.65 or more and 0.87 or less. The ratio (A/B) can be in the range, thereby not only providing a catalyst which is excellent in conversion rate of a raw material in catalytic gas phase oxidation of olefin (hereinafter, sometimes simply referred to as "conversion rate") and which can allow for production of unsaturated aldehyde and unsaturated carboxylic acid at high selectivities, but also resulting in tendencies to enhance the strength of the catalyst and to suppress powdering.

Hereinafter, the ratio (A/B) will be described in more detail. The cumulative pore volume (A) reflects the volume of each pore in the vicinity of the surface of the catalyst, and the cumulative pore volume (B) reflects the volume of each pore in the interior of the catalyst. In other words, a smaller cumulative pore volume (A), while meaning a higher density of the surface of the catalyst and imparting a higher catalyst strength, causes a raw material gas to hardly reach the interior of the catalyst and causes a catalytically active component present in the interior of the catalyst to hardly contribute to a catalyst reaction, resulting in a reduction in conversion rate. A larger cumulative pore volume (A), while meaning a lower density of the surface of the catalyst and causing deterioration in catalyst strength, allows a raw material gas to easily reach the interior of the catalyst and allows any catalytically active component present in not only the vicinity of the surface of the catalyst, but also the interior of the catalyst, to be effectively utilized, thereby resulting in an enhancement in conversion rate.

In the case where the ratio (A/B) is in the range, the balance between the conversion rate of a raw material and the strength of the catalyst is optimized.

The pulverization condition A of the catalyst means pulverization performed by charging 100 g of the catalyst into a tumbling granulator which includes a cylindrical body vertically secured and a disk horizontally disposed at a lower end of the cylindrical body and which allows for rotation movement and revolution movement of a particle by rotation of the disk around the center of the cylindrical body, starting the operation of the disk at a relative centrifugal acceleration of 12 G and accelerating it to a relative centrifugal acceleration of 130 G over 1 minute, and continuing rotation of the disk at a relative centrifugal acceleration of 130 G for 2 minutes.

The relative centrifugal acceleration is defined as a numerical value expressed as the ratio of the magnitude of a centrifugal force applied to a unit weight of the catalyst, to gravity acceleration, and is represented by the following Equation (X):

$$F=1118 \times r \times N^2 \times 10^{-8} \qquad \text{Equation (X)}$$

F: relative centrifugal acceleration (G),
r: distance (cm) from center of rotation to lower end of cylindrical body,
N: rate of rotation (rpm).

Pulverization of the catalyst under the pulverization condition A is specifically performed by, for example, charging 100 g of the catalyst into Marmelizer QJ-230T-2 Model manufactured by DALTON Corporation (cylinder diameter 23 cm), starting the operation at a rate of rotation of 300 rpm and accelerating it to a rate of rotation of 1000 rpm over 1 minute, and continuing running at a rate of rotation of 1000 rpm for 2 minutes.

The cumulative pore volume can be measured according to a mercury intrusion technique. The mercury intrusion technique is a method including subjecting a sample to a decompression treatment under reduced pressure (50 μmHg or less) for 10 minutes, then measuring a mercury intrusion exit curve by use of AutoPore IV 9520 Model manufactured by Micromeritics Japan G.K., and determining the total (cumulative pore volume) of pore volumes.

Furthermore, the conversion rate of a raw material (olefin), the selectivity of unsaturated aldehyde and the selectivity of unsaturated carboxylic acid are calculated according to the following equations.

Conversion rate of olefin(mol %)=(Molar number of olefin reacted/Molar number of olefin fed)×100

Selectivity of unsaturated aldehyde(mol %)=(Molar number of unsaturated aldehyde produced/Molar number of olefin reacted)×100

Selectivity of unsaturated carboxylic acid(mol %)= (Molar number of unsaturated carboxylic acid produced/Molar number of olefin reacted)×100

The cumulative pore volume (A) of pores having a pore diameter of 1 μm or more and 100 μm or less is 0.12 ml/g or more and 0.19 ml/g or less, preferably 0.12 ml/g or more and 0.18 ml/g or less, more preferably 0.15 ml/g or more and 0.18 ml/g or less. The cumulative pore volume (A) is the upper limit or less, thereby allowing breakage and pulverization of the catalyst to be suppressed. The cumulative pore volume (A) is the lower limit or more, thereby allowing a high conversion rate of a raw material, and high selectivity of unsaturated aldehyde, high selectivity of unsaturated carboxylic acid, and a high selectivity ratio of unsaturated carboxylic acid to be easily realized.

The selectivity ratio of unsaturated carboxylic acid here means the selectivity ratio of unsaturated carboxylic acid relative to the total of the selectivity of unsaturated aldehyde and the selectivity of unsaturated carboxylic acid.

The catalyst preferably includes molybdenum (Mo), bismuth (Bi), cobalt (Co), nickel (Ni) and iron (Fe), and the atomic ratio among molybdenum (Mo), bismuth (Bi), cobalt (Co), nickel (Ni) and iron (Fe) in the catalyst preferably satisfies the following Formula (1):

$$Mo_aBi_bCo_cNi_dFe_e \quad (1)$$

wherein a to e represent the atomic ratio with respect to each of elements, and ranges of b=0.5 to 7, c=0.1 to 10, d=0.1 to 10 and e=0.05 to 5 are satisfied when a=12.

The Formula (1) can be satisfied, thereby imparting an excellent conversion rate of propylene and allowing for production of unsaturated aldehyde such as acrolein and unsaturated carboxylic acid such as acrylic acid at high selectivities.

Furthermore, the catalyst preferably includes a carrier. The carrier is preferably inert to a reaction of catalytic gas phase oxidation of olefin and oxygen-containing gas. Examples of the carrier include silica, silicon carbide, alumina, mullite, and alundum, and alumina is further preferable. The catalyst can include the carrier, thereby exerting a catalytic function in not only the surface of the catalyst, but also the interior of the catalyst, and allowing enhancements in selectivity of unsaturated aldehyde and selectivity of unsaturated carboxylic acid to be expected.

The amount of the carrier corresponds to an amount so that the ratio of the amount of a catalytically active component powder to the total of the amount of the catalytically active component powder and the amount of the carrier (the amount of the catalytically active component powder/(the amount of the catalytically active component powder+the amount of the carrier)) is usually 10% by weight to 90% by weight, preferably 30% by weight to 80% by weight. The ratio is in the range, thereby allowing the cumulative pore volume (A) of the catalyst produced, to easily fall within the range of the present invention.

In addition, examples of the shape of the catalyst include a ring shape, a columnar shape, a tablet shape and a spherical shape, and a spherical shape is preferable. Such a spherical shape can mean not only a geometrically true spherical shape, but also an elliptical shape, and is more preferably a shape close to a true spherical shape. In the present embodiment, a catalyst whose particle has a ratio of the longest diameter (major axis diameter) to the shortest diameter (minor axis diameter), among three diameters perpendicular to one another, of 2 or less, preferably 1.3 or less, is defined as having a spherical shape. The catalyst can have a spherical shape, thereby allowing an increase in pressure loss of a catalyst-packed layer in a fixed-bed reactor to be suppressed.

The ratio of the major axis diameter to the minor axis diameter of the catalyst can be obtained by measuring the major axis diameter and the minor axis diameter with respect to each of 100 catalyst particles by a high precision two-dimensional measuring device VM-8040 manufactured by KEYENCE CORPORATION and then determining the average value of the major axis diameter and the average value of the minor axis diameter to calculate the ratio thereof.

Furthermore, the powdering rate of the catalyst is preferably 3.0% or less, more preferably 1.0% or less. In the case where the powdering rate is in the range, the catalyst can be excellent in strength and thus be packed in a reaction tube of a fixed-bed reactor with neither being powdered nor being cracked.

The powdering rate of the catalyst can be determined by, for example, inserting a funnel (150 mm in diameter at the upper section of the cone, and 25 mm in diameter at the lower section of the cone) into the upper section of an acrylic cylinder (φ66 mm) having a height of 1 m, charging about 20 g of the catalyst (powdering rate measurement sample) through the upper section of the cone of the funnel, dropping it through the cylinder onto a tray disposed at the lower section of the cylinder, recovering the powdering rate measurement sample dropped, from the tray, sifting the sample recovered, by a sieve having an aperture of 2.36 mm, to provide a fine particle, measuring the weight (powdered weight) of the fine particle, and performing calculation according to the following equation.

Powdering rate (%)=(Powdered weight/Weight of powdering rate measurement sample)×100

Next, a suitable method for producing the catalyst will be described.

The method for producing the catalyst preferably includes the following two steps.

Step (a): integrating and heating respective source compounds of elements including molybdenum, bismuth, cobalt, nickel, and iron (hereinafter, sometimes referred to as "catalytically active elements") in an aqueous system, thereby providing a catalytically active component powder Step (b); molding the catalytically active component powder obtained in step (a), thereby providing a molded product The integrating of respective source compounds of catalytically active elements including molybdenum, bismuth, cobalt, nickel, and iron in an aqueous system in step (a) means that aqueous solutions or aqueous dispersions of the respective source compounds of catalytically active elements are collectively or stepwise mixed and then subjected to an aging treatment. Specifically, the following (a1) to (a5) methods are adopted, and all the methods are encompassed in the concept of the integrating of the respective source compounds of catalytically active elements in an aqueous system.

(a1) Method including collectively mixing the respective source compounds (a2) Method including collectively mixing the respective source compounds and subjecting the compounds to an aging treatment (a3) Method including stepwise mixing the respective source compounds (a4) Method including repeating a cycle including stepwise mixing the respective source compounds and subjecting the compounds to an aging treatment (a5) Method where the (a1) to (a4) are combined The aging here refers to an "operation including treating an industrial raw material or a half-finished product under particular conditions of a certain time, a certain temperature, or the like for achievement and enhancement of required physical properties or chemical properties or for progression of a predetermined reaction" (Kagaku Daijiten (Encyclopaedia Chimica), Kyoritsu Shuppan Co., Ltd.). In the present invention, the certain time refers to a range from 10 minutes to 24 hours, and the certain temperature refers to a range from room temperature to the boiling point of each of the aqueous solutions or each of the aqueous dispersions.

The heating in step (a) refers to a heating treatment for formation of a composite metal oxide from individual metal oxide of the respective source compounds of catalytically active elements, for formation of a composite metal oxide from a composite compound produced by integration of the respective source compounds of catalytically active elements, for formation of a final composite metal oxide produced, or the like. The heating is not necessarily performed only once. That is, the heating can be arbitrarily performed between and/or in the middle of the respective stages in integration shown in the above (a1) to (a5), or may be, if necessary, additionally performed after such integration. The heating temperature is usually in a range from 200° C. to 600° C.

Drying, pulverizing, and the like may be, if necessary, further performed before or after, and/or in the middle of the integration and the heating.

Examples of the source compound of molybdenum (Mo) include ammonium paramolybdate, molybdenum trioxide, molybdic acid, ammonium phosphomolybdate, and phosphomolybdic acid.

Examples of the source compound of bismuth (Bi) include bismuth chloride, bismuth nitrate, bismuth oxide, and bismuth subcarbonate. The amount of the source compound of bismuth to be charged is preferably an amount so that the resulting catalyst satisfies the Formula (1) where b=0.5 to 7, more preferably b=0.7 to 5.0, further preferably b=1.0 to 4.9, in a=12. The range of b can be as described above, thereby allowing the catalyst to be high in conversion rate, selectivity of unsaturated aldehyde, selectivity of unsaturated carboxylic acid, and selectivity ratio of unsaturated carboxylic acid.

Examples of the source compound of cobalt (Co) include cobalt nitrate, cobalt sulfate, cobalt chloride, cobalt carbonate, and cobalt acetate. The amount of the source compound of cobalt to be charged is preferably an amount so that the resulting catalyst satisfies the Formula (1) where c=0.1 to 10, more preferably c=0.3 to 5.0, further preferably c=0.5 to 3.0, in a=12. The range of c can be as described above, thereby allowing the catalyst to be high in conversion rate, selectivity of unsaturated aldehyde, selectivity of unsaturated carboxylic acid, and selectivity ratio of unsaturated carboxylic acid.

Examples of the source compound of nickel (Ni) include nickel nitrate, nickel sulfate, nickel chloride, nickel carbonate, and nickel acetate. The amount of the source compound of nickel to be charged is preferably an amount so that the resulting catalyst satisfies the Formula (1) where d=0.1 to 10, more preferably d=0.3 to 8, further preferably d=0.5 to 5, in a=12. The range of d can be as described above, thereby allowing the catalyst to be high in conversion rate, selectivity of unsaturated aldehyde, selectivity of unsaturated carboxylic acid, and selectivity ratio of unsaturated carboxylic acid.

Examples of the source compound of iron (Fe) include ferric nitrate, ferric sulfate, ferric chloride, and ferric acetate. The amount of the source compound of iron to be charged is preferably an amount so that the resulting catalyst satisfies the Formula (1) where e=0.05 to 5, more preferably e=0.1 to 3, further preferably e=0.2 to 2, in a=12. The range of e can be as described above, thereby allowing the catalyst to be high in conversion rate, selectivity of unsaturated aldehyde, selectivity of unsaturated carboxylic acid, and selectivity ratio of unsaturated carboxylic acid.

The catalyst preferably further includes sodium (Na), potassium (K), and silicon (Si). That is, the catalyst preferably includes molybdenum (Mo), bismuth (Bi), cobalt (Co), nickel (Ni), iron (Fe), sodium (Na), potassium (K) and silicon (Si), and the atomic ratio among molybdenum (Mo), bismuth (Bi), cobalt (Co), nickel (Ni), iron (Fe), sodium (Na), potassium (K) and silicon (Si) in the catalyst preferably satisfies the following Formula (2):

$$Mo_a Bi_b Co_c Ni_d Fe_e Na_f K_g Si_h \qquad (2)$$

wherein a to h represent the atomic ratio with respect to each of elements, ranges of f=0 to 2, g=0 to 2, and h=0 to 70 are satisfied in a=12, b to e are the same as b to e in the Formula (2) and preferable modes thereof are also the same as in the Formula (1).

Examples of the source compound of sodium (Na) include sodium chloride, sodium carbonate, sodium nitrate, sodium sulfate, sodium acetate, and sodium borate. The amount of the source compound of sodium is preferably an amount so that the resulting catalyst satisfies the Formula (2) where f=0 to 2, more preferably f=0.1 to 1, further preferably f=0.2 to 0.5, in a=12. The value of f can be the lower limit or more, thereby allowing the catalyst to be high in selectivity of unsaturated aldehyde, selectivity of unsaturated carboxylic acid, and selectivity ratio of unsaturated carboxylic acid, and the value of f can be the upper limit or less, thereby allowing the catalyst to be excellent in conversion rate.

Examples of the source compound of potassium (K) include potassium nitrate, potassium sulfate, potassium chloride, potassium carbonate, and potassium acetate. The amount of the source compound of potassium to be charged is preferably an amount so that the resulting catalyst satisfies the Formula (2) where g=0 to 2, more preferably g=0.05 to 1, further preferably g=0.05 to 0.5, in a=12. The value of g can be the lower limit or more, thereby allowing the catalyst to be high in selectivity of unsaturated aldehyde, selectivity of unsaturated carboxylic acid, and selectivity ratio of unsaturated carboxylic acid, and the value of g can be the upper limit or less, thereby allowing the catalyst to be excellent in conversion rate.

Examples of the source compound of silicon (Si) include silica, granular silica, colloidal silica, and fumed silica. The amount of the source compound of silicon is preferably an amount so that the resulting catalyst satisfies the Formula (2) where h=0 to 70, more preferably h=5 to 50, further preferably h=10 to 30, in a=12. The value of h can be the lower limit or more, thereby allowing the catalyst to be favorable in dispersibility of each component, and also be excellent in conversion rate. The value of h can be the upper limit or less, thereby allowing the catalyst to keep the balance between the content of silicon and the contents of other metals and to be excellent in conversion rate.

Step (b) is a step of molding the catalytically active component powder obtained in step (a), thereby providing a molded product. The catalytically active component powder in step (a), while has catalytic activity as it is, is preferably molded because the catalyst is generally packed in a fixed-bed reactor and used for catalytic gas phase oxidation. Such molding into the catalyst can result in an enhancement in workability during packing in and extracting from the reactor and thus suppress an increase in pressure loss in catalytic gas phase oxidation. In the case where the catalyst obtained by molding has a spherical shape, the average diameter of the catalyst is preferably 2 mm to 15 mm, more preferably 3 mm to 10 mm.

The average diameter of the catalyst can be obtained by measuring the average diameter with respect to each of 100 catalyst particles by a high precision two-dimensional measuring device VM-8040 manufactured by KEYENCE CORPORATION and determining the average value thereof.

The method of molding the catalytically active component powder may be any conventionally known method, and examples thereof include the following two methods. One method is a method including allowing a carrier to flow and, at the same time, feeding the catalytically active component powder to the flowing carrier, to thereby support the catalytically active component powder onto the surface of the carrier, and performing granulation and molding to provide a molded product (hereinafter, sometimes referred to as "tumbling granulation method"). Another method is a method including placing the catalytically active component powder into a mold and mechanically pressing it for granulation and molding to thereby provide a molded product (hereinafter, sometimes referred to as "tableting method").

It is preferable in the tumbling granulation method to use a binder in order to facilitate supporting of the catalytically active component powder onto the carrier and enhance the strength of the catalyst produced. Examples of the carrier for use in the tumbling granulation method include a spherical carrier preferably having a major axis diameter of 2.5 mm to 10 mm, further preferably 2.5 mm to 6 mm, such as silica, silicon carbide, alumina, mullite, and alundum. In particular, the porosity of the carrier is preferably 20% to 60%, more preferably 30% to 57%, further preferably 40% to 55%. The water absorption rate of the carrier is preferably 10% to 60%, more preferably 12% to 50%, further preferably 15% to 40%. The porosity and the water absorption rate of the carrier can be in the ranges, thereby not only allowing the catalytically active component to be easily supported onto the carrier, but also allowing the cumulative pore volume (A) of the catalyst produced to easily fall within the range in the present invention, and allowing the ratio (A/B) of the cumulative pore volume (A) to the cumulative pore volume (B) of a pulverized product obtained by pulverization of the catalyst to be easily adjusted within the range in the present invention.

The tumbling granulation method is, for example, a method including rotating a flat or uneven disk located at the bottom of a fixed container included in a granulator, at a high rate, thereby vigorously stirring the carrier in the container due to repeating of rotation movement and revolution movement, and adding thereto the catalytically active component powder, and suitably an additive such as a binder, a molding aid, and/or a strength increase material, thereby supporting the catalytically active component powder onto the carrier. Examples of the method of adding the additive include (1) a method including mixing the catalytically active component powder and the like with the additive to prepare a homogeneous mixture, and charging the homogeneous mixture into a granulator and stirring it, (2) a method including charging the catalytically active component powder and the like and at the same time the additive into a granulator, and stirring the resultant, (3) a method including stirring the catalytically active component powder and the like in a granulator, thereafter charging the additive into the granulator, and further stirring the resultant, (4) a method including adding the additive to the catalytically active component powder and the like to prepare a non-homogeneous mixture, charging the non-homogeneous mixture into a granulator, and stirring the resultant, (5) a method including stirring the catalytically active component powder and the like, and the additive, which are each divided and being charged into a granulator simultaneously, alternately, or in random order. A method can also be arbitrarily adopted where the methods (1) to (5) are appropriately combined for addition in the total amount. In particular, the method (5) is preferably performed, for example, with the rate of addition being regulated by use of an automatic feeder so that a predetermined amount of the catalytically active component powder and the like is supported onto the carrier with neither attachment of the catalytically active component powder to a wall of the fixed container nor aggregation of the catalytically active component powder. In addition, the method (5) is particularly preferable in that not only the cumulative pore volume (A) of the catalyst produced easily falls within the range in the present invention, but also the ratio (A/B) of the cumulative pore volume (A) to the cumulative pore volume (B) of a pulverized product obtained by pulverization of the catalyst is easily adjusted within the range in the present invention.

Examples of the binder include organic binders such as ethanol, glycerin and polyvinyl alcohol, and inorganic binders such as an aqueous silica sol solution, and organic binders are preferable, glycerin and polyvinyl alcohol are further preferable, and glycerin is particularly preferable. Such an organic binder, while may be used as it is, is preferably used in the form of an aqueous solution from the viewpoint of workability. The concentration of the aqueous solution is usually 0.1% by weight or more, preferably 2% by weight to 50% by weight, more preferably 3% by weight to 50% by weight, further preferably 5% by weight to 50% by weight, particularly preferably 7% by weight to 50% by weight. The amount of the binder to be used is usually 0.1 parts by weight to 50 parts by weight, preferably 0.5 parts by weight to 20 parts by weight based on 100 parts by weight of the catalytically active component powder, and is preferably 1% by weight to 40% by weight, more preferably 2% by weight to 35% by weight, further preferably 7% by weight to 30% by weight, particularly preferably 10% by weight to 28% by weight, relative to the catalyst. The binder, in particular, such an organic binder is used at the above concentration of the aqueous solution and in the above amount to be used, thereby not only allowing the cumulative pore volume (A) of the catalyst produced to easily fall within the range in the present invention, but also allowing the ratio (A/B) of the cumulative pore volume (A) to the cumulative pore volume (B) of a pulverized product obtained by pulverization of the catalyst to be easily adjusted within the range in the present invention.

Examples of the molding aid include silica, diatomaceous earth, alumina, glass, and a cellulose powder. Such a molding aid may be used singly or in combination of a plurality thereof, and is preferably used in combination of a plurality thereof. The amount of the molding aid to be used is usually 1 part by weight to 20 parts by weight based on 100 parts by weight of the catalytically active component powder. Furthermore, it is useful for an enhancement in strength of the catalyst to use, if necessary, a strength increase material of an inorganic fiber such as a ceramic fiber or a whisker. The amount of the strength increase material to be used is usually 0.5 parts by weight to 20 parts by weight based on 100 parts by weight of the catalytically active component powder.

It is preferable in the tumbling granulation method to perform granulating under a high load, in order that the cumulative pore volume (A) of pores having a pore diameter of 1 μm or more and 100 μm or less, in the catalyst, is in a particular range, and the ratio (A/B) of the cumulative pore volume (A) to the cumulative pore volume (B) of pores having a pore diameter of 1 μm or more and 100 μm or less, in a pulverized product not passing through a Tyler 6 mesh, in a pulverized product obtained by pulverization of the catalyst is in a particular range. Such a high load means an enhancement in impact strength between the catalytically active component powder and the carrier and an increase in attachment strength between the catalytically active component powder and the carrier in supporting of the catalytically active component powder onto the carrier. It is presumed that the catalytically active component can consequently less penetrate into pores of the carrier to thereby allow the ratio (A/B) to be in a particular range and allow the cumulative pore volume (A) to be in a particular range.

Furthermore, the time taken for granulating depends on the granulating scale and tends to be longer as the granulating scale is larger, and the time is preferably, in the following order, 1 minute to 140 minutes, 1 minute to 130 minutes, 1 minute to 120 minutes, 1 minute to 110 minutes, 1 minute to 100 minutes, 1 minute to 95 minutes, 1 minute to 90 minutes, 1 minute to 85 minutes, 1 minute to 80 minutes, 1 minute to 70 minutes, 1 minute to 60 minutes, 1 minute to 50 minutes, 1 minute to 40 minutes. The time can be in the range, thereby allowing the ratio (A/B) to be in a particular range. The upper limit of the granulating time can be set to the above time, thereby preventing the cumulative pore volume (A) of the catalyst from being decreased due to excessive progression of consolidation on the surface of the catalyst, and thus allowing the cumulative pore volume (A) to be in a particular range.

The granulating condition in the tumbling granulation method can be set to a high load, thereby allowing the catalytically active component to be intensively supported onto the surface of the carrier and decreasing the granulating time, thereby resulting in a thinner catalyst-packed layer in the fixed-bed reactor.

Furthermore, it is important for control of the cumulative pore volume (A) of pores having a pore diameter of 1 μm or more and 100 μm or less, in the catalyst, to understand affinity between the carrier and the catalytically active component powder. The carrier is generally high in water absorption rate, and has so-called hydrophilicity. The catalytically active component powder, when having the same degree of hydrophilicity, easily penetrates also into pores of the carrier and makes control of the cumulative pore volume difficult. Accordingly, penetration of the catalytically active component powder into the carrier can be controlled by appropriately selecting a compound low in solubility in water, as each of the source compounds in step (a), and modulating hydrophilicity of the catalytically active component powder. Examples of the compound low in solubility in water include bismuth subcarbonate and bismuth oxide.

The carrier for use in the tableting method is silica, silicon carbide, alumina, mullite, alundum, or the like, and the size of the carrier is preferably the same as that of the catalytically active component powder. It is preferable to use a binder and a molding aid in order to facilitate supporting of the catalytically active component powder onto the carrier and enhance the mechanical strength of the catalyst produced. It is preferable to further use a pore-imparting material, and the pore-imparting material can be used to thereby control the cumulative pore volume (A) of pores having a pore diameter of 1 μm or more and 100 μm or less, in the catalyst produced. It is preferable in the tableting method to sufficiently mix the binder, the pore-imparting material, and the like with the catalytically active component powder and the like in advance and thereafter mold the mixture to provide a molded product.

The binder and the molding aid for use in the tableting method are preferably the same as the binder and the molding aid for use in the tumbling granulation method, respectively, in terms of the types, the usage modes and the amounts.

Examples of the pore-imparting material include an organic compound, and a cellulose powder, polyvinyl alcohol, and glycerin are preferably used. The pore-imparting material is released from a powder formed by exposure to a high temperature and decomposition and/or burning, during firing of the powder foiled, thereby here imparting pores.

The pressure in tableting in the tableting method is preferably set to a low pressure in order that the cumulative pore volume (A) of pores having a pore diameter of 1 μm or more and 100 μm or less, in the catalyst, is controlled. It is noted that the pressure is needed to be set to a proper pressure in consideration of the strength of the catalyst produced.

The molded product provided by molding the catalytically active component powder in step (b) can be then dried and fired to thereby provide the catalyst. The pore-imparting material is released from such a catalyst particle due to evaporation and/or burning in firing, and pores are here foiled in the catalyst particle. The firing temperature is usually 250° C. to 800° C., preferably 300° C. to 600° C., and the firing time is 1 hour to 50 hours. Such a firing step is preferably performed under air flow in order to rapidly remove a pore-imparting material released from the catalyst particle. Thus, a catalyst which has high strength with many pores being formed can be obtained. Moreover, a catalyst uniformly fired can be obtained by rapidly removing any gas generated from the catalyst particle and feeding air to the catalyst particle. If the air flow is not sufficiently fed, the catalyst is broken due to the change in pressure in release of the pore-imparting agent, and thus not only deteriorated in strength, but also deteriorated in conversion rate, selectivity of unsaturated aldehyde, and selectivity of unsaturated carboxylic acid.

The catalyst thus produced is fed to a fixed-bed reactor, and is used for a reaction for producing unsaturated aldehyde and unsaturated carboxylic acid, such as acrolein and acrylic acid, by catalytic gas phase oxidation of olefin such as propylene, and oxygen-containing gas. The content of the olefin in the gas fed to the fixed-bed reactor is preferably in a range from 5% by volume to 15% by volume, and the space velocity of the olefin is preferably in a range from 50 $h^{-1}$ to 320 $h^{-1}$, more preferably in a range from 80 $h^{-1}$ to 320 $h^{-1}$.

The space velocity is here a value represented by the following equation.

Space velocity SV($h^{-1}$)=Volumetric flow rate of olefin gas to be fed to reactor(under conditions of 0° C. and 1 atm)/Volume of catalyst packed in reactor(not including any solid having no reactivity)

For example, a reaction for producing acrolein and acrylic acid by catalytic gas phase oxidation of propylene and oxygen-containing gas is conducted by feeding a gas having a composition including 5% by volume to 15% by volume of propylene, 5% by volume to 18% by volume of molecular oxygen, 0 to 40% by volume of steam and 20% by volume to 70% by volume of an inert gas such as nitrogen or carbon dioxide gas to the fixed-bed reactor where the catalyst produced as above is packed. The reaction conditions preferably include a temperature range from 300° C. to 450° C., a pressure of ordinary pressure to 150 kPa, and a contact time with the catalyst, of 0.5 seconds to 5 seconds.

EXAMPLES

Hereinafter, the present invention will be more specifically described in detail with reference to Examples, but the present invention is not limited to such Examples.

<Measurement of Supporting Ratio>

Thirty catalyst particles were collected and the total weight was measured (weight A). Thirty carrier particles were collected and the total weight was measured (weight B). The supporting ratio was calculated according to the following equation.

Supporting ratio (%)=(weight$A$−weight$B$)/weight$A$×100

<Measurement of Pore Distribution Spectrum and Cumulative Pore Volume>

A sample was subjected to a decompression treatment under reduced pressure (50 μmHg or less) by use of Auto-Pore IV 9520 Model manufactured by Micromeritics Japan G.K., for 10 minutes, and the cumulative pore volume of pores having a pore diameter of 1 μm or more and 100 μm or less was determined from a mercury intrusion exit curve obtained.

<Measurement of Major Axis Diameter, Minor Axis Diameter, and Average Diameter of Catalyst>

One hundred catalyst particles were collected, the major axis diameter, the minor axis diameter, and the average diameter of each of the particles were measured by a high precision two-dimensional measuring device VM-8040 manufactured by KEYENCE CORPORATION, and thereafter the average major axis diameter, the average minor axis diameter, and the average diameter with respect to such 100 particles were calculated. Furthermore, the ratio of the average major axis diameter to the average minor axis diameter was calculated, and the shape of the catalyst was evaluated.

<Measurement of Powdering Rate of Catalyst>

The catalyst was sifted by a sieve having an aperture of 2.36 mm, and one present on the sieve was adopted as a powdering rate measurement sample. A funnel (150 mm in diameter at the upper section of the cone, and 25 mm in diameter at the lower section of the cone) was inserted into an acrylic cylinder (φ66 mm) having a height of 1 m, and a tray was disposed at the lower section of the cylinder. About 20 g of the powdering rate measurement sample was accurately weighed, charged through the upper section of the cone of the funnel, and dropped through the cylinder onto the tray. The powdering rate measurement sample dropped was recovered from the tray, and sifted by a sieve having an aperture of 2.36 mm, to provide a fine particle, and the weight (powdered weight) of the fine particle was measured to calculate the powdering rate of the catalyst according to the following equation.

Powdering rate (%)=(Powdered weight/Weight of powdering rate measurement sample)×100

Example 1

<Preparation of Catalyst>

A catalytically active component was prepared according to the procedure described in Examples of JP 2017-176931 A. The catalytically active component was fired under an air atmosphere at 440° C. for 6 hours, pulverized, and mixed with 5 parts by weight of cellulose and 5 parts by weight of a glass powder as molding aids based on 100 parts by weight of the catalytically active component, thereby providing a powder including the catalytically active component (hereinafter, referred to as "powder A").

A supported molded product was prepared using the powder A, an aqueous 30% by weight glycerin solution, a spherical carrier mainly including alumina and silica, according to a tumbling granulation method. Specifically, 150 g of a spherical carrier (porosity 50%, water absorption rate 20%) having a diameter of 4.0 mm was loaded to Marmelizer QJ-230T-2 Model manufactured by DALTON Corporation (cylinder diameter 23 cm), and rotated at 150 rpm. Next, alternate addition of the powder A and an aqueous glycerin solution was repeated for 16 minutes, thereby supporting the powder A onto the carrier, to provide a supported molded product. The amount of the aqueous glycerin solution here used was 71 parts by weight based on 100 parts by weight of the powder A.

The supported molded product was dried, and fired in a cylindrical container under air flow at 505° C. for 2 hours, thereby providing a catalyst A. The ratio of the average major axis diameter to the average minor axis diameter of the catalyst A was 1.095, the shape of the catalyst could be determined to be a spherical shape, and the average diameter was 5.53 mm. The powdering rate of the catalyst A was measured, and the results were summarized in Table 1.

The cumulative pore volume (A) of pores having a pore diameter of 1 μm or more and 100 μm or less, in the catalyst A, was 0.174 ml/g. The supporting ratio of the catalyst A was 54%. The atomic ratio of catalytically active elements in the catalyst A was as follows.

Mo/Bi/Co/Ni/Fe=12/2.9/3.4/3.4/0.8

<Pulverization of Catalyst A>

One hundred g of the catalyst A was placed in Marmelizer QJ-230T-2 Model manufactured by DALTON Corporation (cylinder diameter 23 cm), the operation was started at 300 rpm, and the rate of rotation was gradually raised to 1000 rpm over 1 minute, thereby performing pulverization for 2 minutes. After termination of the operation, a massive substance remaining on the cylinder of the Marmelizer was taken out, and sifted by a Tyler 6 mesh. The cumulative pore volume (B) of pores having a pore diameter of 1 µm or more and 100 µm or less, in the pulverized product on the sieve, was 0.213 ml/g. From the foregoing, the ratio (A/B) of the cumulative pore volume (A) to the cumulative pore volume (B) was 0.82.

<Catalytic Gas Phase Oxidation Reaction of Propylene>

Forty ml of the catalyst A was mixed with 52 ml of a mullite ball, the resulting mixture was packed in a reaction tube made of stainless steel, equipped with a niter jacket, a mixed gas of raw materials including 10% by volume of propylene, 17% by volume of steam, 15% by volume of oxygen and 58% by volume of nitrogen was introduced into the reaction tube at a pressure of 70 kPa, and an oxidation reaction of propylene was performed. The space velocity of propylene was here 50 $h^{-1}$. The results were summarized in Table 1.

The conversion rate of propylene and the selectivity of (acrolein+acrylic acid) are defined as follows.

Conversion rate of propylene(mol %)=(Molar number of propylene reacted/Molar number of propylene fed)×100

Selectivity of acrolein(mol %)=(Molar number of acrolein produced/Molar number of propylene reacted)×100

Selectivity of acrylic acid(mol %)=(Molar number of acrylic acid produced/Molar number of propylene reacted)×100

Example 2

A catalytically active component was prepared according to the procedure described in Examples of JP 2017-176931 A. The catalytically active component, without being fired and pulverized, was mixed with 5 parts by weight of cellulose and 5 parts by weight of a glass powder as molding aids based on 100 parts by weight of the catalytically active component, thereby providing a powder including the catalytically active component (hereinafter, referred to as "powder B").

A supported molded product was prepared using the powder B, an aqueous 30% by weight glycerin solution, a carrier mainly including alumina and silica, according to a tumbling granulation method. Specifically, 5 kg of a spherical carrier (porosity 50%, water absorption rate 20%) having a diameter of 4.0 mm was charged into an inclined rotating pan type rolling granulator having a cylinder diameter of 58 cm, and rotated at 30 rpm in the state where the bottom was inclined at 45 degrees relative to a horizontal location. Next, alternate addition of the powder B and an aqueous glycerin solution was repeated for 80 minutes, thereby supporting the powder B onto the carrier, to provide a supported molded product. The amount of the aqueous glycerin solution here used was 34 parts by weight based on 100 parts by weight of the powder B.

The supported molded product was dried, and fired in a cylindrical container under air flow at 505° C. for 2 hours, thereby providing a catalyst B. The ratio of the average major axis diameter to the average minor axis diameter of the catalyst B was 1.071, the shape of the catalyst could be determined to be a spherical shape, and the average diameter was 5.40 mm. The powdering rate of the catalyst B was measured, and the results were summarized in Table 1.

The cumulative pore volume (A) of pores having a pore diameter of 1 µm or more and 100 µm or less, in the catalyst B, was 0.135 ml/g. The supporting ratio of the catalyst B was 54%. The atomic ratio of catalytically active elements in the catalyst B was as follows.

Mo/Bi/Co/Ni/Fe=12/2.9/3.4/3.4/0.8

The catalyst B was pulverized under the same conditions as in Example 1. The cumulative pore volume (B) of pores having a pore diameter of 1 µm or more and 100 µm or less, in the pulverized product on the sieve, was 0.210 ml/g. From the foregoing, the ratio (A/B) of the cumulative pore volume (A) to the cumulative pore volume (B) was 0.64.

The catalyst B was used to perform an oxidation reaction of propylene under the same conditions as in Example 1. The results were summarized in Table 1.

Example 3

A supported molded product was prepared using the powder A prepared in Example 1, an aqueous 30% by weight glycerin solution, a carrier mainly including alumina and silica, according to the tumbling granulation method under the conditions described in Example 1. The amount of the carrier here used was 500 g, the amount of the aqueous glycerin solution based on 100 parts by weight of the powder A was 56 parts by weight, and the granulating time was 30 minutes.

The supported molded product was dried, and fired in a cylindrical container under air flow at 505° C. for 2 hours, thereby providing a catalyst C. The ratio of the average major axis diameter to the average minor axis diameter of the catalyst C was 1.070, the shape of the catalyst could be determined to be a spherical shape, and the average diameter was 5.48 mm. The powdering rate of the catalyst C was measured, and the results were summarized in Table 1.

The cumulative pore volume (A) of pores having a pore diameter of 1 µm or more and 100 µm or less, in the catalyst C, was 0.145 ml/g. The supporting ratio of the catalyst C was 55%. The atomic ratio of catalytically active elements in the catalyst C was as follows.

Mo/Bi/Co/Ni/Fe=12/2.9/3.4/3.4/0.8

The catalyst C was pulverized under the same conditions as in Example 1. The cumulative pore volume (B) of pores having a pore diameter of 1 µm or more and 100 µm or less, in the pulverized product on the sieve, was 0.215 ml/g. From the foregoing, the ratio (A/B) of the cumulative pore volume (A) to the cumulative pore volume (B) was 0.67.

The catalyst C was used to perform an oxidation reaction of propylene under the same conditions as in Example 1. The results were summarized in Table 1.

Comparative Example 1

A supported molded product was prepared using the powder A prepared in Example 1, an aqueous 30% by weight glycerin solution, a carrier mainly including alumina and silica, according to the tumbling granulation method under the conditions described in Example 2. The amount of the carrier here used was 10 kg, the amount of the aqueous glycerin solution based on 100 parts by weight of the powder A was 31 parts by weight, and the granulating time was 140 minutes.

The supported molded product was dried, and fired in a cylindrical container under air flow at 505° C. for 2 hours, thereby providing a catalyst D. The ratio of the average major axis diameter to the average minor axis diameter of the catalyst D was 1.068, the shape of the catalyst could be determined to be a spherical shape, and the average diameter was 5.44 mm. The powdering rate of the catalyst D was measured, and the results were summarized in Table 1.

The cumulative pore volume (A) of pores having a pore diameter of 1 μm or more and 100 μm or less, in the catalyst D, was 0.046 ml/g. The supporting ratio of the catalyst D was 57%. The atomic ratio of catalytically active elements in the catalyst D was as follows.

Mo/Bi/Co/Ni/Fe=12/2.9/3.4/3.4/0.8

The catalyst D was used to pulverize the catalyst under the same conditions as in Example 1. The cumulative pore volume (B) of pores having a pore diameter of 1 μm or more and 100 μm or less, in the pulverized product on the sieve, was 0.208 ml/g. From the foregoing, the ratio (A/B) of the cumulative pore volume (A) to the cumulative pore volume (B) was 0.22.

The catalyst D was used to perform an oxidation reaction of propylene under the same conditions as in Example 1. The results were summarized in Table 1.

Comparative Example 2

A supported molded product was prepared using the powder A prepared in Example 1, an aqueous 30% by weight glycerin solution, a carrier mainly including alumina and silica, according to the tumbling granulation method under the conditions described in Example 1. The amount of the carrier here used was 200 g, the amount of the aqueous glycerin solution based on 100 parts by weight of the powder A was 61 parts by weight, and the granulating time was 15 minutes.

The supported molded product was dried, and fired in a sagger installed in a muffle furnace at 505° C. for 2 hours, thereby providing a catalyst E. The ratio of the average major axis diameter to the average minor axis diameter of the catalyst E was 1.079, the shape of the catalyst could be determined to be a spherical shape, and the average diameter was 5.54 mm. The powdering rate of the catalyst E was measured, and the results were summarized in Table 1.

The cumulative pore volume (A) of pores having a pore diameter of 1 μm or more and 100 μm or less, in the catalyst E, was 0.191 ml/g. The supporting ratio of the catalyst E was 54%. The atomic ratio of catalytically active elements in the catalyst E was as follows.

Mo/Bi/Co/Ni/Fe=12/2.9/3.4/3.4/0.8

The catalyst E was used to pulverize the catalyst under the same conditions as in Example 1. The cumulative pore volume (B) of pores having a pore diameter of 1 μm or more and 100 μm or less, in the pulverized product on the sieve, was 0.216 ml/g. From the foregoing, the ratio (A/B) of the cumulative pore volume (A) to the cumulative pore volume (B) was 0.88.

The catalyst E was used to perform an oxidation reaction of propylene under the same conditions as in Example 1. The results were summarized in Table 1.

TABLE 1

| | | | | Oxidation reaction of propylene | | | |
|---|---|---|---|---|---|---|---|
| | Powdering rate of catalyst (%) | Space velocity ($h^{-1}$) | Reaction temperature (° C.) | Conversion rate of propylene (mol %) | Selectivity of acrolein (mol %) | Selectivity of acrylic acid (mol %) | Selectivity of (acrolein + acrylic acid) (mol %) |
| Example 1 | 0.2 | 100 | 340 | 97.6 | 70.8 | 22.6 | 93.4 |
| Example 2 | 0.6 | 100 | 340 | 97.3 | 72.4 | 21.2 | 93.6 |
| Example 3 | 0.8 | 100 | 340 | 98.1 | 67.9 | 24.0 | 91.9 |
| Comparative Example 1 | 0.0 | 100 | 340 | 97.0 | 65.5 | 26.6 | 92.1 |
| Comparative Example 2 | 8.4 | 100 | 340 | 97.7 | 63.1 | 26.8 | 89.9 |

The invention claimed is:

1. A catalyst for producing unsaturated aldehyde and unsaturated carboxylic acid,
wherein the catalyst comprises molybdenum (Mo), bismuth (Bi), cobalt (Co), nickel (Ni) and iron (Fe), wherein
a cumulative pore volume (A) is based on pores having a pore diameter of 1 to 100 μm in the catalyst prior to pulverization,
a cumulative pore volume (B) is based on pores having a pore diameter of 1 to 100 μm, in a pulverized product not passing through a Tyler 6 mesh after pulverization,
the cumulative pore volume (A) is 0.12 ml/g or more and 0.19 ml/g or less, and
the ratio (A/B) of the cumulative pore volume (A) to the cumulative pore volume (B) in a pulverized product obtained by pulverization of the catalyst under a pulverization condition A is 0.30 or more and 0.87 or less;
Pulverization condition A
one hundred g of the catalyst is charged into a tumbling granulator which comprises a cylindrical body vertically secured and a disk horizontally disposed at a lower end of the cylindrical body and which allows for rotation movement and revolution movement of a particle by rotation of the disk around the center of the cylindrical body, operation of the disk is started at a relative centrifugal acceleration of 12 G and accelerated to a relative centrifugal acceleration of 130 G over 1 minute, and rotation of the disk is continued at a relative centrifugal acceleration of 130 G for 2 minutes; wherein
the relative centrifugal acceleration is defined as a numerical value expressed as the ratio of the magnitude of a centrifugal force applied to a unit weight of the catalyst, to gravity acceleration, and is represented by the following Equation (X):

$$F = 1118 \times r \times N^2 \times 10^{-8} \qquad \text{Equation (X)}$$

F: relative centrifugal acceleration (G),
r: distance (cm) from center of rotation to lower end of cylindrical body,
N: rate of rotation (rpm).

2. The catalyst according to claim 1, wherein the catalyst comprises molybdenum (Mo), bismuth (Bi), cobalt (Co), nickel (Ni), and iron (Fe), and the atomic ratio among molybdenum (Mo), bismuth (Bi), cobalt (Co), nickel (Ni), and iron (Fe) in the catalyst satisfies the following Formula (1):

$$Mo_a Bi_b Co_c Ni_d Fe_e \tag{1}$$

wherein a to e represent the atomic ratio with respect to each of elements, a=12, b=0.5 to 7, c=0.1 to 10, d=0.1 to 10 and e=0.05 to 5.

3. The catalyst according to claim 2, wherein the catalyst consists essentially of molybdenum (Mo), bismuth (Bi), cobalt (Co), nickel (Ni), and iron (Fe).

4. The catalyst according to claim 2, wherein the catalyst consists of molybdenum (Mo), bismuth (Bi), cobalt (Co), nickel (Ni), and iron (Fe).

5. The catalyst according to claim 1, wherein the catalyst comprises a carrier.

6. The catalyst according to claim 1, wherein the catalyst has a spherical shape.

7. A method for producing acrolein and acrylic acid, comprising:
    performing catalytic gas phase oxidation of propylene and oxygen-containing gas by using the catalyst according to claim 1.

* * * * *